United States Patent [19]

Tsujino et al.

[11] Patent Number: 5,413,938

[45] Date of Patent: May 9, 1995

[54] REAGENT FOR MEASURING IMMATURE LEUKOCYTES

[75] Inventors: Yukio Tsujino, Kobe; Takashi Morikawa; Yukio Hamaguchi, Both of Akashi, all of Japan

[73] Assignee: Tao Medical Electronics Co., Ltd., Hyogo, Japan

[21] Appl. No.: 214,248

[22] Filed: Mar. 17, 1994

[30] Foreign Application Priority Data

Mar. 19, 1993 [JP] Japan .................. 5-60037

[51] Int. Cl.$^6$ ............ G01N 33/52; G01N 33/49
[52] U.S. Cl. .................... 436/63; 435/2; 435/40.51; 356/36; 356/39; 436/175; 436/176; 436/825
[58] Field of Search ............ 435/2; 424/3; 356/36, 356/39; 436/8, 10, 17, 175, 176, 825

[56] References Cited

U.S. PATENT DOCUMENTS

| | | | |
|---|---|---|---|
| 4,099,917 | 7/1978 | Kim | 436/17 |
| 4,751,179 | 6/1988 | Ledis et al. | 435/34 |
| 5,250,437 | 10/1993 | Toda et al. | 436/10 |
| 5,258,315 | 11/1993 | Vormbrock | 436/174 |

FOREIGN PATENT DOCUMENTS

WO8809504 1/1988 Japan .

3252556 11/1991 Japan .

*Primary Examiner*—David A. Redding
*Attorney, Agent, or Firm*—Birch, Stewart, Kolasch & Birch

[57] ABSTRACT

A reagent for measuring immature leukocytes which comprises: (1) a polyoxyethylene-based nonionic surfactant having the general formula (I) in a sufficient amount capable of fixing cytoplasms and cell membranes of immature leukocytes:

$$R_1-R_2-(CH_2CH_2O)_n-H \qquad (I)$$

where $R_1$ is an alkyl, alkenyl or alkynyl group having 10 to 25 carbon atoms; $R_2$ is $-O-$, $-(C_6H_4)-O-$ or $-COO-$; and n is an integer of 10 to 40, (2) a solubilizing agent in a sufficient amount capable of damaging cell membranes of blood cells other than immature leukocytes and shrinking them, (3) an amino acid in a sufficient amount capable of stabilizing cytoplasm and cell membrane of immature leukocytes, and (4) an aqueous medium, which adjusts pH value in the range of 5.0 to 9.0, osmolarity in the range of 150 to 600 mOsm/kg and electric conductivity in the range of 6.0 to 9.0 mS/cm, respectively.

14 Claims, 4 Drawing Sheets

REAGENT FOR MEASURING IMMATURE LEUKOCYTES

BACKGROUND OF THE INVENTION

1. Field of the Invention

The invention relates to a reagent for classification and counting immature cells contained in a liquid sample such as blood.

2. Description of the Related Art

Various blood cells such as erythrocytes, leukocytes and platelets are included in peripheral blood of normal subject. The blood cells are produced in a bone marrow and transferred to a blood stream, while growing in accordance with differentiating themselves from immature cells.

For example, leukocytes such as neutrophils, eosinophils and basophils are differentiated from immature cells to mature cell through (myeloblast→promyelocyte→myelocyte→metamyelocyte) to (stab cell→segmented cell). In a peripheral blood collected from a normal subject, immature cells such as myeloblasts, promyelocytes, myelocyte and metamyelocyte do not appear and stab cells are a small number. However, immature leukocytes appear in some specific cases of, for example, bloods collected from patients suffering blood diseases such as leukemia, metastasis of cancer to bone marrow and severe infectious disease. Thus, it is important and significant to measure immature leukocytes for diagnosis of such diseases.

As one technique for an automated classification and counting of blood cells, there is known a method of recording images of cells and processing. In other case, blood cells are automatically classified and counted by passing them suspended in a diluent through an aperture and processing signals obtained from the respective corpuscles. Lately, the latter's flow system is preferably used in view of accuracy, cost or the like.

According to the flow system, blood cells are suspended in a diluent, and detected by signals based on the respective cells, for example, by signals based on the difference in an optical property and an electric property. That is, they may be detected by using a flow cytometry for detecting scattered light or fluorescent light based on the difference in an optical property, or by using a blood cell counter for detecting electric signals generated from blood cells when the blood cells pass through an aperture therein to which is applied an electric current based on the difference in an electric property. The latter can be further classified into either a DC method for applying direct current to detect signals based on the difference in electric resistance of blood cells and an RF method for applying high frequency current in several MHz to detect signals based on the difference in dielectric constant of blood cells. The DC method detects signals sized in proportion to the volume of the cells, while the RF method detects signals reflecting information on internal structure (the size of nucleus) and constituting substances of the cells.

For example, (1) WO88/09504 and (2) European Patent Application No. 044240 A1 describe a combination of the DC method and the RF method for classification and counting 5 types of leukocytes and abnormal cells.

The above quoted reference (1) describes the classification and counting of 5 types of normal (mature) leukocytes i.e., lymphocytes, monocytes, neutrophils, eosinophils and basophils, and abnormal cells using polyoxyethylene-based nonionic surfactant or polyoxyethylene-based anionic surfactant. For example, FIG. 18 illustrates the distribution of lymphoblasts n, myeloblasts l, other immature granulocytes k and left shifted distribution j, where it seems that the left shift means the increase of neutrophils showing fewer nuclear segmentation (stab cell neutrophils).

The reference (2) describes the classification and counting of 5 types of leukocytes and other abnormal cells using polyoxyethylene-based nonionic surfactant under an acidic and hypotonic conditions. FIG. 5 illustrates the distribution of abnormal cells e such as leukemic cells.

In the meanwhile, a variety of diluents and preservative solutions for blood are also known. For example, there are known preservative solutions containing amino acids, which act to adsorb on outer membrane of cell and maintain its morphology (cell protection).

The references (1) and (2) have the drawbacks that there remain unclassified immature cells and there is insufficient accuracy of classification because they primarily aim to classify mature leukocytes into five types and immature cells are additionally classified and counted. For example, when only a polyoxyethylene-based nonionic surfactant is used, mature leukocytes and immature leukocytes are not clearly differentiated because of insufficient shrinkage of mature leukocytes and insufficiently lysing of erythrocytes.

SUMMARY OF THE INVENTION

The present invention provides a reagent for measuring immature leukocytes which comprises:

(1) a polyoxyethylene-based nonionic surfactant having the general formula (I) in a sufficient amount capable of fixing cytoplasms and cell membranes of immature leukocytes:

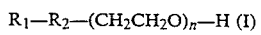

$$R_1-R_2-(CH_2CH_2O)_n-H \quad (I)$$

where $R_1$ is an alkyl, alkenyl or alkynyl group having 10 to 25 carbon atoms; $R_2$ is $-O-$, $-(C_6H_4)-O-$ or $-COO-$; and n is an integer of 10 to 40, (2) a solubilizing agent in a sufficient amount capable of damaging cell membranes of blood cells other than immature leukocytes and shrinking them, (3) an amino acid in a sufficient amount capable of stabilizing cytoplasms and cell membranes of immature leukocytes, and (4) an aqueous medium, which adjusts pH value in the range of 5.0 to 9.0, osmolarity in the range of 150 to 600 mOsm/Kg and electric conductivity in the range of 6.0 to 9.0 mS/cm, respectively.

An object of the present invention is to provide a reagent which improves an accuracy of classification and counting of immature cells.

DETAILED DESCRIPTION OF THE PREFERRED EMBODIMENT

Figure 1:
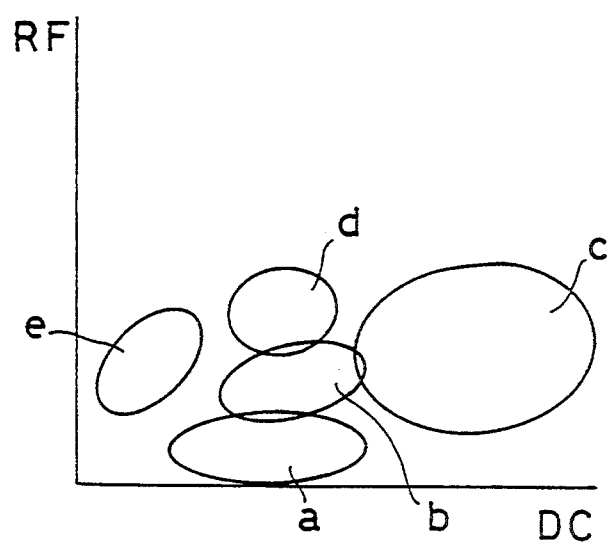
FIG. 1 schematically shows a two dimensional scattergram with axes of DC signal intensity and RF signal intensity when a blood sample is measured using a reagent of the present invention.

The polyoxyethylene-based nonionic surfactant used in the present invention is a surfactant which is capable of fixing cytoplasms and cell membranes of immature leukocytes and represented by the general formula (I)

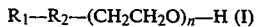

$$R_1-R_2-(CH_2CH_2O)_n-H \quad (I)$$

where $R_1$ is an alkyl, alkenyl group or alkynyl group having 10 to 25 carbon atoms; $R_2$ is —O—, —($C_6H_4$)—O— or —COO—; and n is an integer of 10 to 40. Preferable examples are those having the formula (I) where $R_1$ is an alkenyl group or an alkynyl group having 10 to 20 carbon atoms, $R_2$ is —O—, and n is an integer of 10 to 30 because such surfactants have two characteristics of lysing erythrocytes and fixing leukocytes in a good balance. More preferably, $C_{18}H_{34}O(CH_2CH_2O)_{16}H$ and $C_{18}H_{34}O(CH_2CH_2O)_{15}H$ are used.

The surfactant may be contained at a concentration of 5 to 50 g/l, more preferably, 20 to 28 g/l in the reagent.

The solubilizing agent contained in the reagent of the present invention is used to damage a cell membrane of blood cells other than immature leukocytes and shrink them.

Examples of the solubilizing agents are:

(1) a sarcosine derivative having the general formula (II):

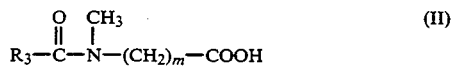

$$R_3-\overset{O}{\underset{\|}{C}}-\overset{CH_3}{\underset{|}{N}}-(CH_2)_m-COOH \quad (II)$$

where $R_3$ is an alkyl group having $C_{10-22}$ carbon atoms, and m is an integer of 1 to 5 or a salt thereof;

(2) a cholic acid derivative having the general formula (III)

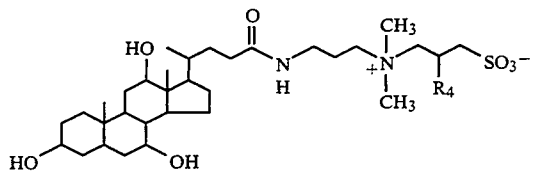

where $R_4$ is a hydrogen atom or a hydroxyl group or a salt thereof;

(3) a methylglucan amide having the general formula (IV):

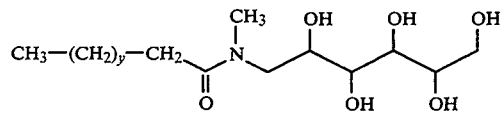

where y is an integer of 5 to 7; and (4) n-octyl β-glucoside, sucrose monocaprate and N-formyl methylleucylalanine.

Specific examples of the solubilizing agents of (1) to (3) described above are: (1) sodium N-lauroylsarcosinate, sodium N-lauroyl-N-methyl-β-alanate and N-lauroylsarcosine; (2) CHAPS (3-[(3-chloramidopropyl)-dimethylammonio]-1-propanesulfonate) and CHAPSO (3-[(3-chloramidopropyl) dimethylammonio]-2-hydroxy-1-propanesulfonate); and (3)MEGA 8 (octanoyl-N-methylglucamide), MEGA 9 (nonanoyl-N-methylglucamide) and MEGA 10 (decanoyl-N-methylglucamide). Among the above solubilizing agents, sodium N-lauroylsarcosinate is preferable.

The concentration of the solubilizing agent can be adjusted in accordance with the type of solubilizing agents. It may be used at a concentration such that erythrocytes ghosts and nuclei naked mature leukocytes can be effectively shrunk. For example, the sarcosine derivative (II) or a salt thereof is used at a concentration of 0.2 to 2.0 g/l; the cholic acid derivative (III) or a salt thereof is used at a concentration of 0.1 to 0.5 g/l; the methylglucan amide (IV) is used at a concentration of 1.0 to 8.0 g/l; and n-octyl β-glucoside, sucrose monocaprate or N-formyl methylleucylalanine is used at a concentration of 0.01 to 50.0 g/l.

The amino acid used in the present invention is those capable of stabilizing cytoplasms and cell membranes of abnormal cells. The amino acid may be any amino acid constituting a protein. The amino acid constituting a protein can be classified into three groups of neutral amino acid, acidic amino acid and basic amino acid as shown in Table 1.

In view of the stabilization and classification of immature cells, a sulfur containing amino acid such as methionine, cystin and cysteine, preferably methionine is used.

The amount of the amino acid to be used for preparing the reagent of the present invention is not specifically limited, and can be adjusted in accordance with the type of the amino acid to be used. For example, glutamic acid which is an acidic amino acid can be preferably used at a concentration of 1 to 50 g/l, more preferably at 8 to 12 g/l, most preferably at 10 g/l. In case of using valine which is a neutral amino acid, it can be preferably used at a concentration of 1 to 50 g/l, more preferably at 8 to 12 g/l, most preferably at 10.0 g/l. Further, methionine is preferably used at a concentration of 1 to 50 g/l, more preferably at a concentration of 16 to 24 g/l.

TABLE 1

| Type | | | Name |
|---|---|---|---|
| Neutral Amino acid | Aliphatic amino acid | | glycine alanine |
| | | Branched amino acid | valine leucine isoleucine |
| | | Hydroxy amino acid | serine threonine |
| | | Sulfur containing amino acid | cystine cysteine methionine |
| | | Acid amide amino acid | asparagine glutamine |
| | Imino acid | | proline |
| | Aromatic amino acid | | phenylalanine tyrosine tryptophan |
| Acidic amino acid | | | aspartic acid glutamic acid |
| Basic amino acid | | | lysine arginine histidine |

The aqueous medium of the present invention includes water, an organic aqueous medium or various buffering solutions such as HEPES and phosphate buffer, and may contain a pH adjusting agent such as sodium hydroxide and an agent for adjusting osmolarity such as a salt when required. The various buffering solutions are preferably used.

The reagent of the present invention may be prepared by a known method using the necessary components as mentioned above. The reagent is usually in the form of aqueous solution. Preferably, pH, osmolarity and electric conductivity of the reagent are adjusted in the range of 5.0–9.0, 150 to 600 mOsm/kg, and 6.0 to 9.0 mS/cm, respectively, for example by adding a pH adjusting agent such as sodium hydroxide or an agent for adjusting osmolarity such as a salt when required.

In order to classify and count immature cells, the thus prepared reagent of the present invention is mixed with a sample including immature leukocytes (in practice, with a blood), whereby the components contained in the reagent of the present invention can be reacted with each of cell groups contained in the sample simultaneously. By mixing the reagent with the sample, a difference is generated to the level that each of the immature leukocyte groups can be distinguished from other cell groups. The mixing is conducted at 25° to 40° C., preferably at 30° to 34° C.

Now the following is discussed on significant mechanism of the reagent of the present invention.

(1) Immature leukocytes seem to be resistant to damage their cell membrane compared with mature leukocytes, upon action of the polyoxyethylene-based nonionic surfactant in the reagent of the invention.

(2) When the cell membrane of immature leukocytes, however, is partially damaged, the amino acid and the nonionic surfactant are believed to invade into the cell through the damaged part and stabilize the cell membrane part and the cell component.

Generally, it is known that the smaller the molar number of addition n of the polyoxyethylene-based nonionic surfactant, the stronger is the hemolytic activity, and the greater the molar number of addition n, the weaker is the hemolytic activity. According to the present invention, it is found that when the molar number of addition n of the polyoxyethylene-based nonionic surfactant is equal to or greater than 10, the surfactant works for stabilizing cells.

It is also generally known that the strength of the cell membrane weakens in the order of mature leukocytes->immature leukocytes>erythrocytes. However, it unexpectedly weakens in the order of immature leukocytes>mature leukocytes>erythrocytes in case of using the reagent of the present invention. Namely, immature leukocytes are harder to damage than mature leukocytes.

When the reagent is mixed with a blood, the following phenomena may occur.

Each of cell groups (for example, immature leukocytes, mature leukocytes and erythrocytes) are damaged, when the reagent of the present invention including polyoxyethylene-based nonionic surfactant is mixed with blood at pH 5.0 to 8.0. The level of the damage depends on the type of cells. That is, the membranes of the erythrocytes are damaged and immediately they are lysed. The membranes of mature leukocytes are damaged and the components therein are eluted from the cell, so that the nuclei are naked. Immature leukocytes are also damaged, but before the components are eluted, the polyoxyethylene-based nonionic surfactant and amino acid invade into the cell from the damaged portion, thereby fixing the cell membrane and components contained therein. As a result, immature leukocytes can be fixed in the state maintaining the membrane and cytoplasm.

In order to classify cells, it is necessary to cause a difference among each of cell groups to the level that each of them can be distinguished from others and to maintain the distinguished state for a certain period. One of the conventional techniques for achieving this purpose is to add a fixing agent to the cells after adding a surfactant. For example, as the fixing agents, formaldehyde and glutaraldehyde are respectively disclosed in U.S. Pat. No. 4,099,917 and 4,751,179. The fixing mechanism of the present invention is different from the conventional one in that the fixing is conducted inside the cell membrane in the present invention, while it is conducted outside the cell membrane in the conventional case.

The conventional method described above cannot clearly distinguish immature leukocytes from mature leukocytes and erythrocyte ghosts. In contrast, the solubilizing agent contained in the reagent of the present invention acts on mature leukocytes and erythrocyte ghosts and classifies them by shrinking erythrocyte ghosts and mature leukocytes of which nuclei are naked.

According to the present invention, immature leukocytes can be stably and accurately classified and counted by causing a difference in morphological features as described above and by individually counting the cells which show the difference.

FIG. 1 illustrates a two-dimensional distribution diagram obtained by performing the DC and RF methods. In FIG. 1, a, b, c and d represent a group of blast cells (a1 denotes granulocytic blast cells and a2 denotes lymphocytic blast cell), myelocytes and metamyelocytes, promyelocytes, stab cells, respectively. The reference letter e represents a group of erythrocyte ghost and mature leukocytes. As seen from the figure, erythrocytes and mature leukocytes are shrunk to a level that each of immature leukocytes can be completely distinguished.

When blood is first mixed with a solution containing an amino acid and then the above described surfactant is added to the mixture, those which are added to blood would be finally the same as the case using the reagent of the present invention. However, if the amino acid is added to the blood in that order, the function as well as the effect of the present invention cannot be exhibited. There is a significant difference between the process above and the present invention in the function and effect. The difference is described in detail hereinafter.

In the former process, amino acid acts on the outside of the cell membrane to keep the morphological features of cells, before the surfactant is added. As a result, cells are already protected by the amino acid when adding the surfactant, so that the surfactant does not function sufficiently. Accordingly, immature leukocytes cannot be classified. For causing a sufficient difference to distinguish immature leukocytes, the cell membrane needs to be damaged before the cell protecting function works on it by the amino acid, and needs to allow the amino acid to invade into the cell at the same time of damaging the membrane. Further, the effect of the present invention is not caused when the amino acid is added after the cell membrane is completely damaged. Therefore, it is important to act the amino acid from the inner side of the cell, not from the outside, so that the amino acid and the above surfactant must be contained in the same solution.

In the case of using the reagent of the present invention, it is possible to employ not only an electric impedance method such as DC method and RF method but also an optical flow cytometry. When a forward scattered light (FSC) and a side scattered light (SSC) are detected, an almost similar scattergram with the intensities of FSC and SSC as the axes can be obtained as shown in FIG. 1. The forward scattered light reflects the volume of cells and the side scattered light reflects inner information (the size of nuclei and degree of complexity). It is understood from the figure that the intensities of DC and RF, respectively, corresponded to the intensities of the forward scattered light and the side scattered light.

Preferred examples of the reagents in accordance with the present invention will be described as follows:

EXAMPLE I

Composition of Reagent

| | | |
|---|---|---|
| (1) Polyoxyethylene-based nonionic surfactant $C_{18}H_{34}$—O—$(CH_2CH_2O)_{16}$—H | 24.0 g | |
| (2) Solubilizing agent (Anionic surfactant) Sodium N-lauroylsarcosinate | 1.5 g | |
| (3) Amino acid (Sulfur containing amino acid) DL-methionine | 20.0 g | |
| (4) Buffer | | |
| HEPES | 12.0 g | |
| NaOH (1 N) | 0.3 g | |
| (5) Osmolarity Adjusting Agent | | |
| NaCl | 4.0 g | |
| (6) Water | 1000 ml | |
| an amount to balance the total amount to | | |

Blood was diluted 256-fold using the reagent of the above composition under the condition of pH=6.8, $\pi$ (osmolarity)=350 mOsm/kg.$H_2O$, $\rho$(electrical conductivity)=7.4 mS/cm, and the solution temperature=33° C. The dilution was incubated for 13 seconds and the particles were measured for 6 seconds by the RF/DC method.

Figure 2:
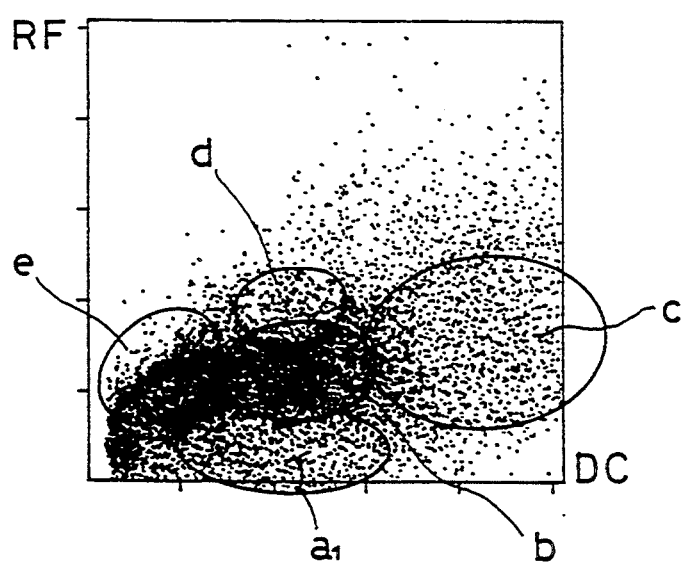
FIG. 2 shows a two dimensional scattergram with axes of DC signal intensity and RF signal intensity when peripheral blood collected from patients suffering from chronic myelocytic leukemia is measured using the reagent of the present invention.
Figure 3:
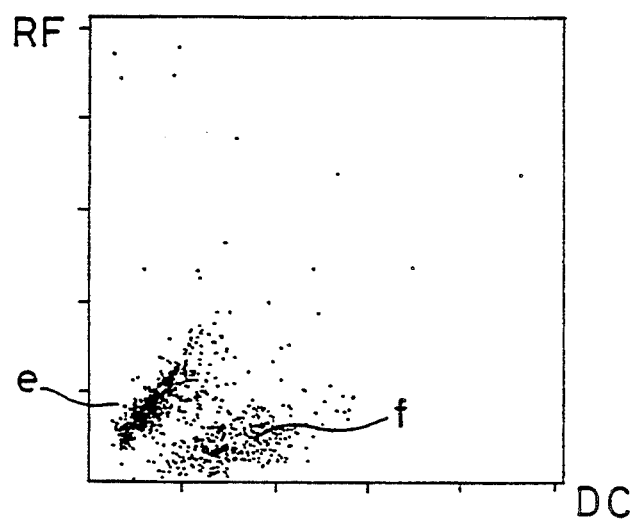
FIG. 3 shows a two dimensional scattergram with axes of DC signal intensity and RF signal intensity when peripheral blood collected from patients having lymphocytic immature cells is measured using the reagent of the present invention.
Figure 4:
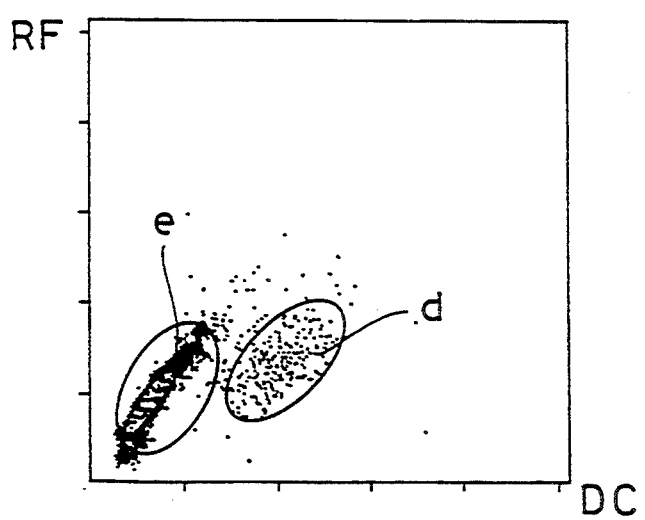
FIG. 4 shows a two dimensional scattergram with axes of DC signal intensity and RF signal intensity when peripheral blood collected from normal subjects is measured using the reagent of the present invention.

FIGS. 2, 3 and 4 show the results of the measurement of different blood samples by a two dimensional scattergram with axes of RF signal intensity and DC signal intensity obtained FIGS. 2, 3 and 4 show the results of the measurement of peripheral blood collected from patients suffering from chronic myelocytic leukemia, patients having lymphocytic immature cells detected, and normal subjects, respectively.

It is observed that the blood sample shown in FIG. 2 contains a number of myeloblasts, myelocytes, metamyelocytes, promyelocytes and stab cells, which were distributed in group a1 for myeloblasts, group b for myelocytes and metamyelocytes, group c for promyelocytes and group d for stab cells. Each of the groups of a1, b, c, and d was confirmed to be myeloblasts, myelocytes, metamyelocytes, promyelocytes and stab cells by measuring each of above fractions separated from blood sample, and by correlation test between measurement using the reagent of the present invention and visual observation. The reference letter e designates a group comprising ghosts of erythrocytes and mature leukocytes. It is understood that all the groups other than immature leukocytes are fully shrunk and do not cause any troubles in classification of immature leukocytes.

The blood sample shown in FIG. 3 contains lymphocytic immature cells (lymphoma cells and atypical lymphocytes) as immature cells, which were distributed in group f. The group f was confirmed to be lymphocytic immature cells by the method similar to the above. The reference letter e designates a group comprising ghosts of erythrocytes and mature leukocytes.

The blood sample shown in FIG. 4 was collected from normal subject. The blood sample only contains stab cells (stab cell neutrophils). The sample did not contain other immature cells. The stab cells were distributed in group d, which is the same region as distributed in FIG. 2.

Figure 5:
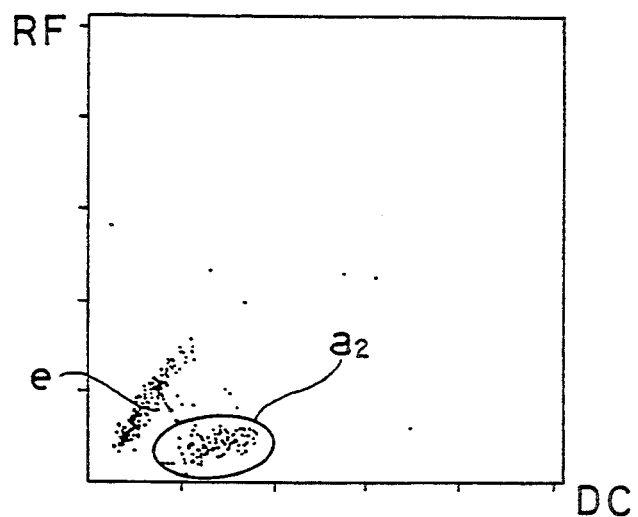
FIG. 5 shows a two dimensional scattergram with axes of DC signal intensity and RF signal intensity when peripheral blood collected from patients suffering from acute lymphocytic leukemia is measured using the reagent of the present invention.
Figure 6:
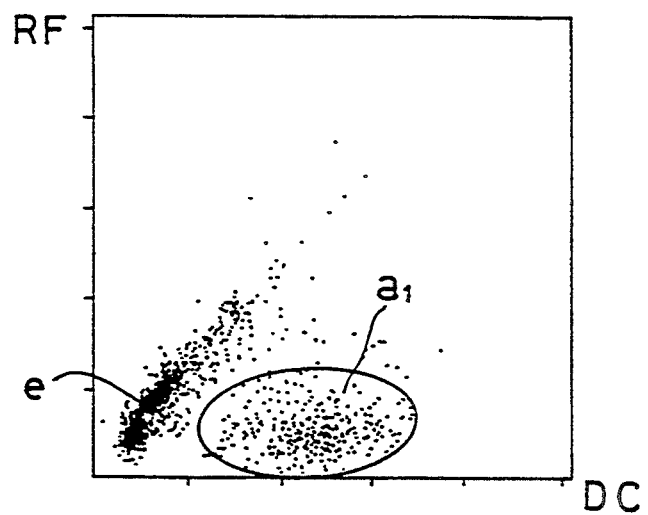
FIG. 6 shows a two dimensional scattergram with axes of DC signal intensity and RF signal intensity when peripheral blood collected from patients suffering from acute myeloid leukemia is measured using the reagent of the present invention.

FIGS. 5 and 6 show the results of the measurement of blood from patients suffering from acute lymphocytic leukemia and patients suffering from acute myeloid leukemia, respectively. Groups a2 and a1 designate lymphoblasts and myeloblasts, respectively. This was confirmed by using a cell sorter.

Thus, immature leukocytes were distinguished from mature leukocytes and classified into blast cells, myelocytes, metamyelocytes, promyelocytes and stab cells. Further, lymphoblasts and myeloblasts can be distinguished..pa
In addition to the composition described above, tests were conducted with each component in various amounts, and preferred effects were exhibited in the following range.

| | |
|---|---|
| (1) $C_{18}H_{34}$—O—$(CH_2CH_2O)_{16}$—H | 5–50 g (20–28 g) |
| (2) Sodium N-lauroylsarcosinate | 0.1–2.0 g (1.2–2.0 g) |
| (3) DL-methionine | 1–50 g (16–24 g) |
| (4) pH | 5.0–10.0 (6.0–8.0) |
| (5) $\pi$ | 150–500 mOsm/kg · $H_2O$ (250–380) |
| (6) $\rho$ | 3.0–12.0 (6.0–9.0) |
| (7) Dilution Ratio | 100–500-fold (200–300) |
| (8) Solution Temperature | 25.0–40.0° C. (30.0–34.0) |

*Parenthesized figures denote more preferable ranges.

Composition of the reagents used in Examples I is listed in Table 2.

TABLE 2

|  | Example I composition | preferable concentration |
|---|---|---|
| polyoxyethylene-based surfactant | $C_{18}H_{34}O(CH_2CH_2O)_{16}H$ 24.0 g | 5–50 (20–28) |
| solubilizing agent | anionic surfactant N-lauro 1.5 g | 0.1–2.0 (1.2–2.0) |
| amino acids | sulfur containing amino acid DL-methionine 20.0 g | 1–50 (16–24) |
| buffer | HEPES 12.0 g 1 N NaOH 0.3 g | pH 5.0–10.0 (6.0–8.0) $\rho$ (mS/cm) 3.0–12.0 (6.0–9.0) |
| osmotic pressure adjusting agent | NaCl 4.0 g | $\pi$ (mOsm/kg · $H_2O$) 150–500 (250–380) |
| water | sufficient for 1000 ml | |

EXAMPLE II

Example II was conducted in the same manner as Example I except that glutamic acid of acidic amino acid was used in place of the amino acid of Example I (sulfur containing amino acid: methionine) in an amount of 10.0 g (at 10.0 g/l). The amount of glutamic acid can be varied in the range of 1 to 50 g, preferably from 8 to 12 g to bring preferred effect.

Composition of the reagents used in Examples II is listed in Table 3.

TABLE 3

|  | Example II composition | preferable concentration |
|---|---|---|
| polyoxyethylene-based surfactant | $C_{18}H_{34}O(CH_2CH_2O)_{16}H$ 24.0 g | 5–50 (20–28) |
| solubilizing agent | anionic surfactant N-lauro 1.5 g | 0.1–2.0 (1.2–2.0) |
| amino acids | acidic amino acid L-gulutamic acid 10.0 g | 1–50 (8–12) |
| buffer | HEPES 12.0 g 1 N NaOH 0.3 g | pH 5.0–10.0 (6.0–8.0) $\rho$ (mS/cm) 3.0–12.0 (6.0–9.0) |
| osmotic pressure adjusting agent | NaCl 4.0 g | $\pi$ (mOsm/kg · $H_2O$) 150–500 (250–380) |
| water | sufficient for 1000 ml | |

EXAMPLE III

Example III was conducted in the same manner as Example I except that valine of branched amino acid was used in place of the amino acid of Example I (sulfur containing amino acid: methionine) in an amount of 10.0 g (at 10.0g/l). The amount of valine can be varied in the range of 1 to 50 g, preferably from 8 to 12 g to bring preferred effect.

Composition of the reagents used in Examples III is listed in Table 4.

TABLE 4

|  | Example III composition | preferable concentration |
|---|---|---|
| polyoxyethylene-based surfactant | $C_{18}H_{34}O(CH_2CH_2O)_{16}H$ 24.0 g | 5–50 (20–28) |
| solubilizing agent | anionic surfactant N-lauro 1.5 g | 0.1–2.0 (1.2–2.0) |

TABLE 4-continued

|  | Example III composition | preferable concentration |
|---|---|---|
| amino acids | aliphatic amino acid L-valine 10.0 g | 1–50 (16–24) |
| buffer | HEPES 12.0 g 1 N NaOH 0.3 g | pH 5.0–10.0 (6.0–8.0) $\rho$ (mS/cm) 3.0–12.0 (6.0–9.0) |
| osmotic pressure adjusting agent | NaCl 4.0 g | $\pi$ (mOsm/kg · $H_2O$) 150–500 (250–380) |
| water | sufficient for 1000 ml | |

EXAMPLE IV

Example IV was conducted in the same manner as Example I except that the polyoxyethylene-based nonionic surfactant and the solubilizing agent were replaced with $C_{18}H_{34}$—O—$(CH_2CH_2O)_{15}$—H and CHAPS, respectively. The $C_{18}H_{34}$—O—$(CH_2CH_2O)_{15}$—H and CHAPS were used in an amount of 5.0 g (at 5.0g/l) and 0.3 g (at 0.3 g/l), respectively. The amount of the $C_{18}H_{34}$—O—$(CH_2CH_2O)_{15}$—H and CHAPS can be varied in the range of 1 to 9 g, preferably 3 to 7 g and in the range of 0.1 to 0.5 g, preferably 0.2 to 0.4 g, respectively to bring preferred effect.

Composition of the reagents used in Examples IV is listed in Table 5.

TABLE 5

|  | Example IV composition | preferable concentration |
|---|---|---|
| polyoxyethylene-based surfactant | $C_{18}H_{34}O(CH_2CH_2O)_{16}H$ 5.0 g | 1–9 (3–7) |
| solubilizing agent | solubilizing agent CHAPS 0.3 g | 0.1–0.5 (0.2–0.4) |
| amino acids | sulfur containing amino acid DL-methionine 20.0 g | 1–50 (16–24) |
| buffer | HEPES 12.0 g 1 N NaOH 0.3 g | pH 5.0–10.0 (6.0–8.0) $\rho$ (mS/cm) 3.0–12.0 (6.0–9.0) |
| osmotic pressure adjusting agent | NaCl 4.0 g | $\pi$ (mOsm/kg · $H_2O$) 150–500 (250–380) |
| water | sufficient for 1000 ml | |

EXAMPLE V

Example V was conducted in the same manner as Example I except that the polyoxyethylene-based nonionic surfactant, solubilizing agent and amino acid were replaced with $C_{18}H_{34}$—O—$(CH_2CH_2O)_{15}$—H, MEGA8 and valine, respectively. The $C_{18}H_{34}$—O—$(CH_2CH_2O)_{15}$—H, MEGA8 and valine were used in an amount of 5.0 g (at 5.0 g/l), 5.0 g ( at 5.0 g/l ) and 20.0 g (20.0 g/l). The amount of $C_{18}H_{34}$—O—$(CH_2CH_2O)_{15}$—H, MEGA8 and valine can be varied in the range of 1 to 9 g, preferably 3 to 7 g, in the range of 1 to 8 g, preferably 4 to 6 g, and in the range of 1 to 50 g, preferably 16 to 24, respectively to bring preferred effect.

When Examples I to V were compared, it can be found that each group of immature leukocytes appeared in the same regions. The results in classification (measured values) were most accurate in Examples I, and the accuracy falls from Example I to V in this order.

Composition of the reagents used in Examples V is listed in Table 6.

TABLE 6

|  | Example V composition | preferable concentration |
|---|---|---|
| polyoxyethylene-based surfactant | $C_{18}H_{34}O(CH_2CH_2O)_{16}H$ 5.0 g | 1–9 (3–7) |
| solubilizing agent | solubilizing agent MEGA 8 5.0 g | 1–8 (4–6) |
| amino acids | L-valine 20.0 g | 1–50 (16–24) |
| buffer | HEPES 12.0 g 1 N NaOH 0.3 g | pH 5.0–10.0 (6.0–8.0) $\rho$ (mS/cm) 3.0–12.0 (6.0–9.0) |
| osmotic pressure adjusting agent | NaCl 4.0 g | $\pi$ (mOsm/kg · H$_2$O) 150–500 (250–380) |
| water | sufficient for 1000 ml | |

Comparative Example I

Figure 7:
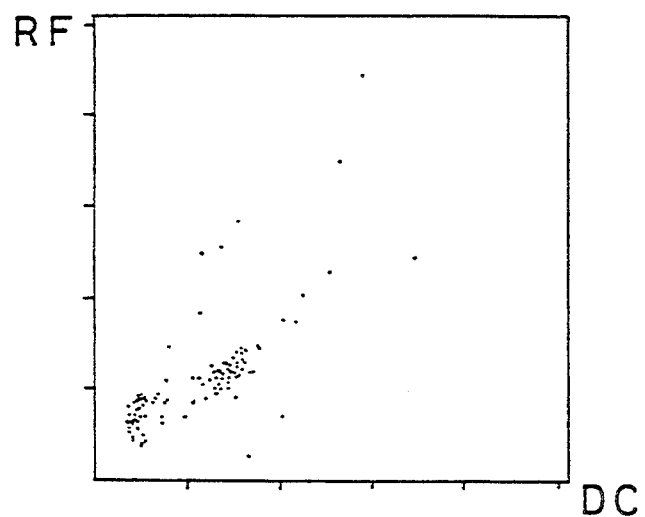
FIG. 7 shows a two dimensional scattergram with axes of DC signal intensity and RF signal intensity measured by Comparative Example I.

The Comparative Example I was conducted in the same manner as Example I except that the polyoxyethylene-based nonionic surfactant is not contained. The result is shown in FIG. 7. As seen from FIG. 7, cell membrane was destroyed and cytoplasm was eluted from the cell.

Comparative Example II

Figure 8:
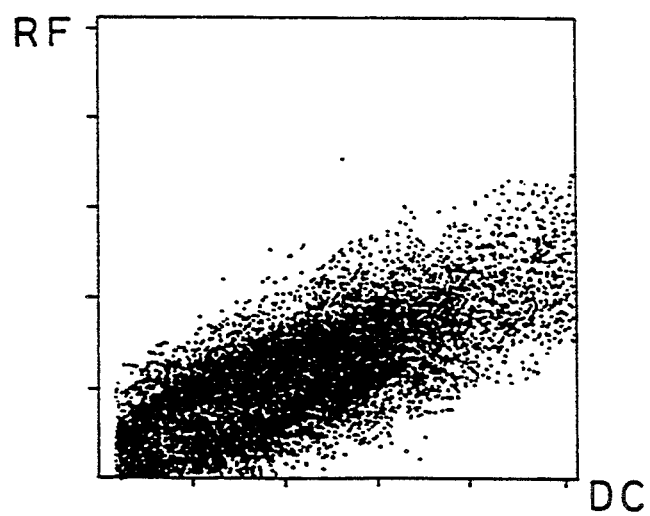
FIG. 8 shows a two dimensional scattergram with axes of DC signal intensity and RF signal intensity measured by Comparative Example II.

The Comparative Example II was conducted in the same manner as Example I except that the solubilizing agent is not contained. The result is shown in FIG. 8. As seen from FIG. 8, although cell membrane and nuclear were stabilized, many of erythrocytes which are not lysed appear.

Composition of the reagents used in Comparative Examples I and II is listed in Table 7.

TABLE 7

|  | Comparative Example I composition |
|---|---|
| solubilizing agent | anionic surfactant N-lauro 1.5 g |
| amino acids | sulfur containing amino acid DL-methionine 20.0 g |
| buffer | HEPES 12.0 g 1 N NaOH 0.3 g |
| osmolarity adjusting agent | NaCl 4.0 g |
| water | sufficient for 1000 ml |
|  | Comparative Example II composition |
| polyoxyethylene-based surfactant | $C_{18}H_{34}O(CH_2CH_2O)_{16}H$ 24.0 g |
| amino acids | sulfur containing amino acid DL-methionine 20.0 g |
| buffer | HEPES 12.0 g 1 N NaOH 0.3 g |
| osmolarity adjusting agent | NaCl 4.0 g |
| water | sufficient for 1000 ml |

According to the present invention, precise subdivision of immature leukocytes is made available.

Since the reagent of the present invention is prepared in a single package, it is preferably applied to an automated analyzer. Moreover, the reagent of the present invention can be applied to not only an apparatus of detecting electric impedance but also an optical apparatus.

What we claimed is:

1. A reagent for measuring immature leukocytes which comprises:

(1) a polyoxyethylene-based nonionic surfactant having the general formula (I) in a sufficient amount capable of fixing cytoplasms and cell membranes of immature leukocytes:

$$R_1-R_2-(CH_2CH_2O)_n-H \quad (I)$$

where $R_1$ is an alkyl, alkenyl or alkynyl group having 10 to 25 carbon atoms; $R_2$ is —O—, —(C$_6$H$_4$)—O— or —COO—; and n is an integer of 10 to 40, (2) a solubilizing agent in a sufficient amount capable of damaging cell membranes of blood cells other than immature leukocytes and shrinking them, (3) an amino acid in a sufficient amount capable of stabilizing cytoplasms and cell membranes of immature leukocytes, and (4) an aqueous medium, which adjusts pH value in the range of 5.0 to 9.0, osmolarity in the range of 150 to 600 mOsm/Kg and electric conductivity in the range of 6.0 to 9.0 mS/cm, respectively.

2. A reagent according to claim 1, in which n of the nonionic surfactant is an integer of 10 to 20.

3. A reagent according to claim 1, in which the solubilizing agent is a sarcosine derivative having the general formula (II):

where $R_3$ is an alkyl group having $C_{10-22}$ carbon atoms, and m is an integer of 1 to 5 or a salt thereof.

4. A reagent according to claim 1, in which the solubilizing agent is a cholic acid derivative having the general formula (III):

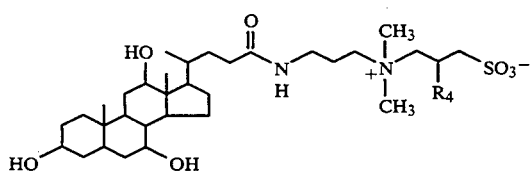

where $R_4$ is a hydrogen atom or a hydroxyl group or a salt thereof.

5. A reagent according to claim 1, in which the solubilizing agent is a methylglucan amide having the general formula (IV):

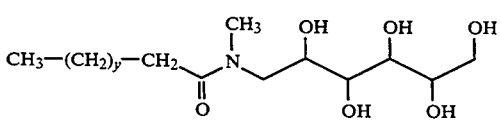

where y is an integer of 5 to 7.

6. A reagent according to claim 1, in which the solubilizing agent is n-octyl β-glucoside, sucrose monocaprate or N-formyl methylleucylalanine.

7. A reagent according to claim 1, in which the amino acid is a sulfur containing amino acid selected from the group consisting of methionine, cystin and cysteine.

8. A reagent according to claim 1, in which the nonionic surfactant is contained at a concentration of 5 to 50 g/l.

9. A reagent according to claim 3, in which the solubilizing agent is contained at a concentration of 0.2 to 2.0 g/l.

10. A reagent according to claim 4, in which the solubilizing agent is contained at a concentration of 0.1 to 0.5 g/l.

11. A reagent according to claim 5, in which the solubilizing agent is contained at a concentration of 1.0 to 8.0 g/l.

12. A reagent according to claim 6, in which the solubilizing agent is contained at a concentration of 0.01 to 50.0 g/l.

13. A reagent according to claim 1, which is an aqueous solution containing 20 to 28 g of $C_{18}H_{34}O(CH_2CH_2O)_{16}H$ as the nonionic surfactant, 1.2 to 2.0 g of sodium N-lauroylsarcosinate as the solubilizing agent and 16 to 24 g of DL-methionine as the amino acid, based on one liter of the solution which is adjusted to show a pH value of 6.0 to 8.0, an osmolarity of 250 to 380 mOsm/kg and an electric conductivity of 6.0 to 9.0 ms/cm.

14. A method for measuring immature leukocytes from a blood sample which comprises contacting said blood sample with a reagent comprising (a) a polyoxyethylene-based nonionic surfactant having the general formula (I) in an amount sufficient to fix cytoplasms and all membranes of immature leukocytes;

wherein $R_1$ is an alkyl, alkenyl, or alkynyl group having 10 to 25 carbon atoms; and $R^2$ is —O—, $(C_6H_4-O)$—, or —COO—; and n is an integer of 10 to 40;

(b) a solubilizing agent in an amount sufficient to damage cell membranes of blood cells other than immature leukocytes;

(c) an amino acid in an amount sufficient to stabilize said cytoplasm and cell membranes of said immature leukocytes; and (d) an aqueous medium; said reagent being capable of adjusting the pH to a range of 5.0 to 9.0, the osmolarity to the range of 150 to 600 in Osm/kg and the electric conductivity to the range of 6.0 to 9.0 mS/cm;

and measuring said immature leukocytes.

* * * * *

UNITED STATES PATENT AND TRADEMARK OFFICE
CERTIFICATE OF CORRECTION

PATENT NO. : 5,413,938
DATED : May 9, 1995
INVENTOR(S) : Tsujino, et. al.

It is certified that error appears in the above-indentified patent and that said Letters Patent is hereby corrected as shown below:

Title page, item [73], Assignee: change "Tao" to --Toa--.

Signed and Sealed this

Second Day of July, 1996

Attest:

BRUCE LEHMAN

Attesting Officer     Commissioner of Patents and Trademarks